US009533144B2

(12) United States Patent
Bahmer

(10) Patent No.: US 9,533,144 B2
(45) Date of Patent: Jan. 3, 2017

(54) STIMULUS SIGNAL FOR SIMULTANEOUS MEASUREMENT OF AUDITORY STEADY STATE RESPONSES AND PSYCHOPHYSICAL PITCH DISCRIMINATION

(71) Applicant: MED-EL Elektromedizinische Geraete GmbH, Innsbruck (AT)

(72) Inventor: Andreas Bahmer, Aschaffenburg (DE)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 14/750,162

(22) Filed: Jun. 25, 2015

(65) Prior Publication Data
US 2015/0374987 A1 Dec. 31, 2015

Related U.S. Application Data

(60) Provisional application No. 62/016,793, filed on Jun. 25, 2014, provisional application No. 62/054,503, filed on Sep. 24, 2014.

(51) Int. Cl.
*A61N 1/36* (2006.01)
*A61N 1/372* (2006.01)
*H04R 25/00* (2006.01)

(52) U.S. Cl.
CPC ....... *A61N 1/36032* (2013.01); *A61N 1/37241* (2013.01); *H04R 25/606* (2013.01); *H04R 25/70* (2013.01); *H04R 2225/67* (2013.01)

(58) Field of Classification Search
CPC ... A61B 5/0482; A61B 5/04845; A61B 5/121; A61B 5/16; A61B 5/7203; A61B 5/7257; A61B 5/726; A61N 1/36032; A61N 1/37241; H04R 2225/67
See application file for complete search history.

(56) References Cited

U.S. PATENT DOCUMENTS

2008/0215332 A1 9/2008 Zeng et al.
2010/0290651 A1 11/2010 Grayden et al.
(Continued)

OTHER PUBLICATIONS

Bahmer, et al, "Recording and online analysis of auditory steady state responses (ASSR) in Matlab", *Journal of Neuroscience Methods*, vol. 187, pp. 105-113 (2010), 9 pages.
(Continued)

*Primary Examiner* — Deborah Malamud
(74) *Attorney, Agent, or Firm* — Sunstein Kann Murphy & Timbers LLP

(57) ABSTRACT

Arrangements are described for fitting a cochlear implant system to an implanted patient. A test stimulation sequence is delivered to the implanted patient which is based on a concatenated sequence of time shifted envelopes of sinusoidal amplitude modulated (SAM) signals that have a carrier frequency $f_c$ modulated by a jittered modulation frequency $f_m + \epsilon$, where $\epsilon$ is a frequency jitter component selected from a jitter range of $[-\epsilon_1, +\epsilon_1]$. Patient responses to the test stimulation sequence are simultaneously measured including an auditory steady-state response (ASSR) measurement signal and a psychophysical pitch discrimination response. The time shifted envelopes are adapted to avoid measurement artifacts in the ASSR measurement signal around the modulation frequency $f_m$.

14 Claims, 11 Drawing Sheets

(56) References Cited

U.S. PATENT DOCUMENTS

2012/0197153 A1* 8/2012 Kraus .................. A61B 5/743
  600/545
2014/0121725 A1 5/2014 Bahmer

OTHER PUBLICATIONS

Hofmann, et al, "Electrically Evoked Auditory Steady State Responses in Cochlear Implant Users", *Journal of the Association of Research in Otolaryngology*, 11:267-282 (2010), 16 pages.
Jeng, et al, "Electrically Evoked Auditory Steady-State Responses in a Guinea Pig Model: Latency Estimates and Effects of Stimulus Parameters", *Audiol Neurotol* 2008:13; pp. 161-171, 11 pages.
International Searching Authority, Authorized Officer Blaine R. Copenheaver, International Search Report and Written Opinion, PCT/US2015/037652, date of mailing Sep. 30, 2015, 15 pages.

\* cited by examiner

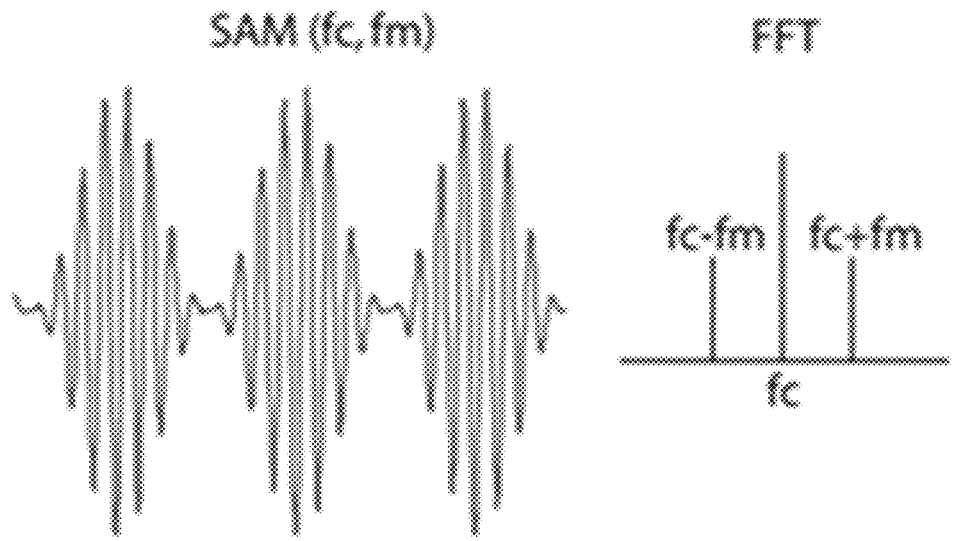
*Fig. 10A*  *Fig. 10B*
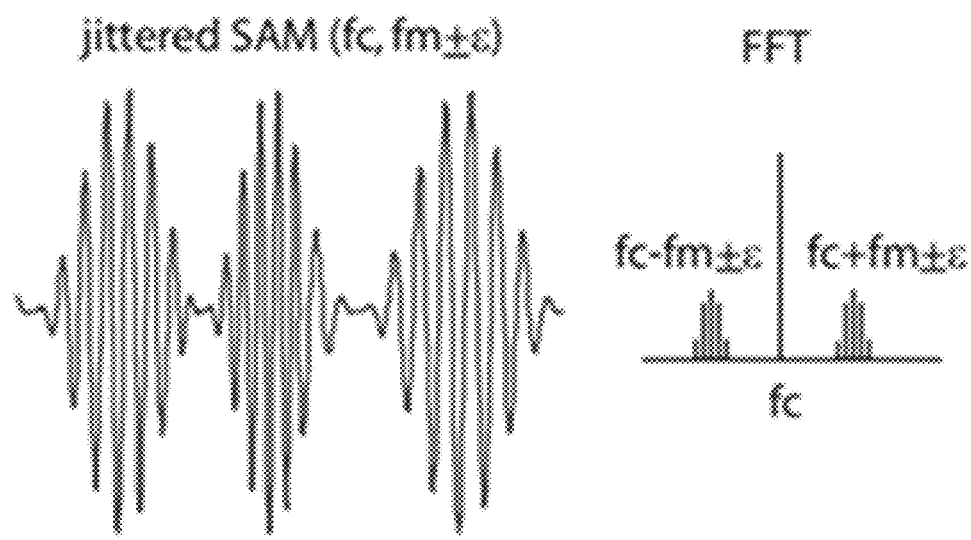
*Fig. 11A*  *Fig. 11B*

STIMULUS SIGNAL FOR SIMULTANEOUS MEASUREMENT OF AUDITORY STEADY STATE RESPONSES AND PSYCHOPHYSICAL PITCH DISCRIMINATION

This application claims priority from U.S. Provisional Patent Application 62/016,793, filed Jun. 25, 2014, and from U.S. Provisional Patent Application 62/054,503, filed Sep. 24, 2014, both of which are incorporated herein by reference.

TECHNICAL FIELD

The present invention relates to evaluation of potential fitting techniques for cochlear implant patients.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through wires in an electrode lead 109 to an implanted electrode array 110.

The electrode array 110 penetrates into the cochlea 104 through a surgical opening called a cochleostomy. The electrode array 110 has multiple electrode contacts 112 on or recessed slightly below its outer surface for applying one or more electrical stimulation signals to target audio neural tissue within the cochlea 104. The extra-cochlear electrode lead 109 that goes from the implant housing 108 to the cochleostomy opening usually has no electrical contacts except perhaps a ground electrode and it encloses connecting wires that deliver electrical stimulation signals to the electrode contacts on the electrode array 110.

After implantation, a cochlear implant system needs to be adjusted for each specific patient in a clinical fitting process. Information on patient performance while using the implant system is needed to compare different processing algorithms and/or processing parameters with regards to any differences in the performance of the system or the experience of the patient. This information can be obtained subjectively by feedback from the patient and/or by different objective measurement methods.

SUMMARY

Embodiments of the present invention include systems and methods for fitting a cochlear implant system to an implanted patient. A test stimulation generator is configured to deliver to the implanted patient a test stimulation sequence based on a concatenated sequence of time shifted envelopes of sinusoidal amplitude modulated (SAM) signals having a carrier frequency $f_c$ modulated by a jittered modulation frequency $f_m+\epsilon$, where $\epsilon$ is a frequency jitter component selected from a jitter range of $[-\epsilon_1,+\epsilon_1]$. A response measurement module is configured to measure patient responses to the test stimulation sequence including an auditory steady-state response (ASSR) measurement signal and a psychophysical pitch discrimination response. The test stimulation generator is configured to adapt the time shifted envelopes to avoid measurement artifacts in the ASSR measurement signal around the modulation frequency $f_m$.

In further specific embodiments, the test stimulation generator may be configured to derive the test sequence by an analog-to-digital sampling of the time shifted envelopes at sampling frequency having a corresponding sampling period. For example, the test stimulation generator may be configured to time shift envelopes of the SAM signals to offset a time mismatch delta representing an accumulated time difference for all preceding envelopes between each envelope duration and a next higher integer multiple of sampling period.

Specific embodiments may also include a correlation evaluation module that is configured to evaluate a correlation between the patient responses to determine an appropriate fitting process for the cochlear implant patient. The correlation evaluation module may include a fitting process selection sub-module that is configured to determine an objective ASSR fitting process as the appropriate fitting process when the correlation is evaluated to be sufficient and/or a subjective psychophysical pitch discrimination fitting process as the appropriate fitting process when the correlation is evaluated to be insufficient.

The ASSR measurement signal may specifically be an acoustically evoked ASSR (AASSR) or an electrically evoked ASSR (EASSR).

BRIEF DESCRIPTION OF THE DRAWINGS

FIG. 10 A-B shows examples of a sinusoidal amplitude modulated (SAM) signal.

FIG. 11 A-B shows examples of a SAM signal with added jitter.

DETAILED DESCRIPTION

Embodiments of the present invention are directed to a pre-fitting evaluation of whether a patient who has received a cochlear implant can be fitted based on an objective electrophysical measurement such as auditory steady-state response (ASSR) measurements, or whether to instead perform the fitting based on state-of-the-art psychophysical or on other objective fitting methods. An electrophysical fitting such as one based on ASSR may be used exclusively or in addition to other standard fitting methods. The pre-fitting test adds a jitter variation component to the test stimulus and then evaluates the correlation between an objective ASSR of a patient and their simultaneous subjective responses to psychophysical measurements.

In the following unless explicitly specified differently, the auditory steady state response ASSR can be either or both electrically evoked ASSR (EASSR) and acoustically evoked ASSR (AASSR). Jitter variation in EASSR means a sequence of stimulus pulses with varied distance (time) between the individual pulses. Jitter variation in AASSR means variation of the test modulation frequencies as explained above.

Figure 1:
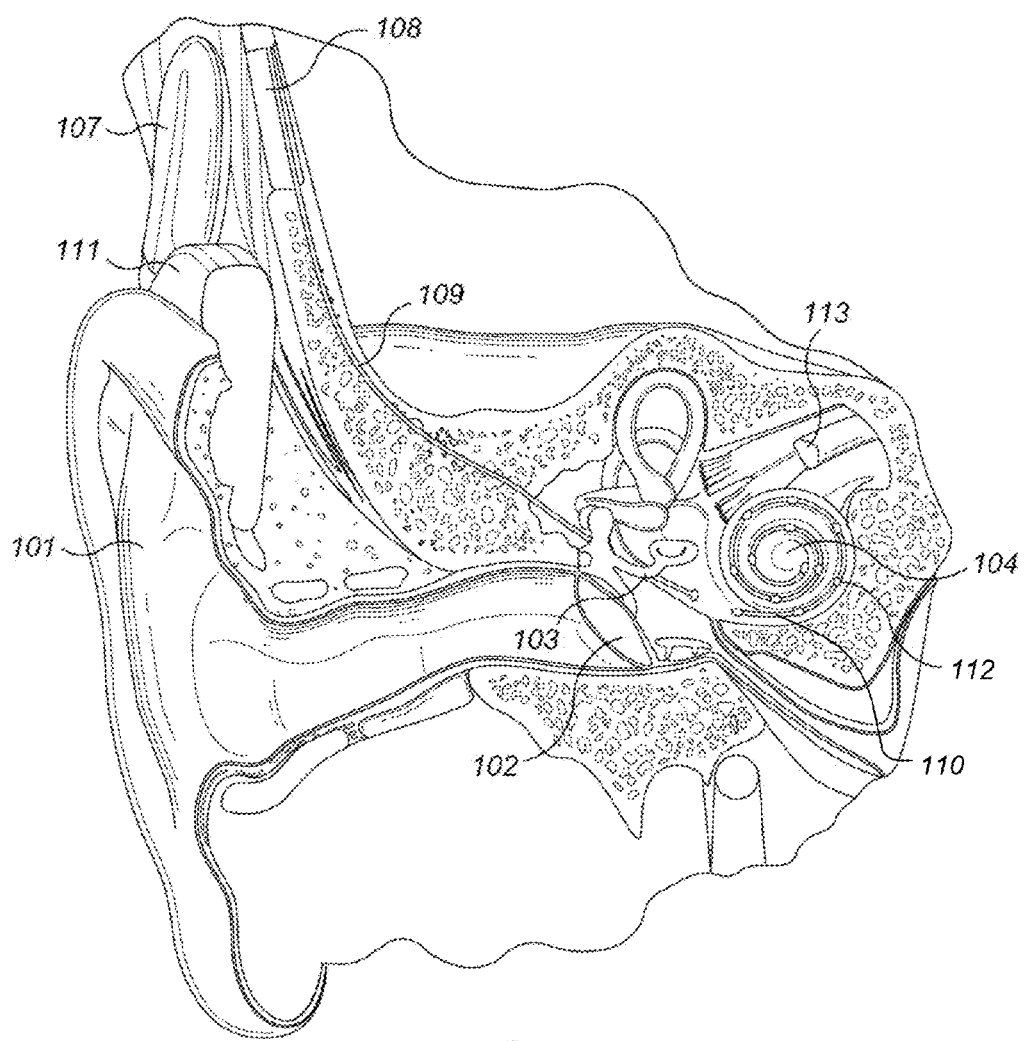
FIG. 1 shows various anatomical structures of the human ear and components of a typical cochlear implant system in relation thereto.
Figure 2:
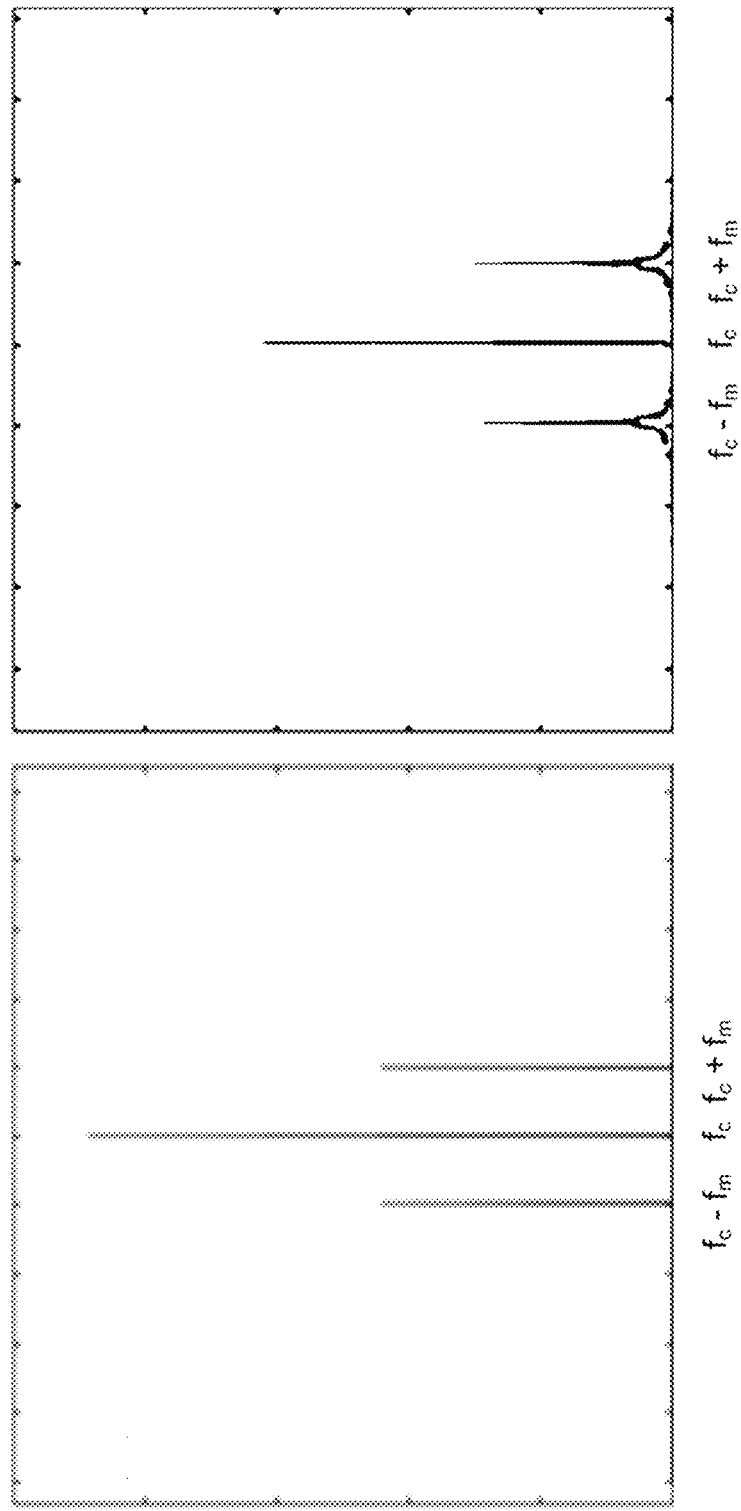
FIG. 2 A-B show spectrum of a sinusoidal amplitude modulated test stimulation signal with and without a jitter component.

In ASSR measurements, neural responses are evoked after application of a sequence of a periodic test stimulation signal. In acoustically evoked ASSR (AASSR), the test stimulation signal may be a sinusoidal amplitude modulated signal (SAM) with a carrier frequency $f_c$ and modulation frequency $f_m$. FIG. 2A shows an example of the corresponding frequency spectrum for such a SAM test stimulation signal in which the carrier frequency $f_c$ determines the specific stimulation location within the cochlea and the modulation frequency $f_m$ (sidebands) determines the temporal fluctuations within the frequency channel in case of unresolved harmonics. FIG. 2B shows the corresponding AASSR frequency spectrum for the case where a jitter component is introduced into the modulation test frequency $f_m$. In electrically evoked ASSR (EASSR), the active electrode contact of the implanted electrode array determines the specific stimulation location within the cochlea and the test stimulation signal may be a periodic pulse train with a repetition rate of the modulation test frequency $f_m$.

When the auditory system receives such a test stimulation signal, the neuronal response signals are locked to the test frequency $f_m$, thereby allowing very frequency-specific objective measurements. (See e.g., Bahmer and Baumann, *Recording and Online Analysis of Auditory Steady State Responses (ASSR) in Matlab*, J. Neurosci. Methods., 2010, 187(1):105-13; Picton et al., *Potentials Evoked by the Sinusoidal Modulation of the Amplitude or Frequency of a Tone*, J. Acoust. Soc. Am., 1987, 82:165-78; Rees et al., *Steady State Evoked Responses to Sinusoidally Amplitude-Modulated Sounds Recorded in Man*, Hear Res. 1986, 23:123-33; Hofmann and Wouters, *Electrically Evoked Auditory Steady State Responses in Cochlear Implant Users*, J. Assoc. Res. Otolaryngol. 2010 June, 11(2):267-82; all of which are incorporated herein by reference in their entireties). Thus embodiments of the present invention provide arrangements to determine the amount of correlation between objective electrophysiologic tests such as ASSR and subjective psychophysical tests.

Figure 3:
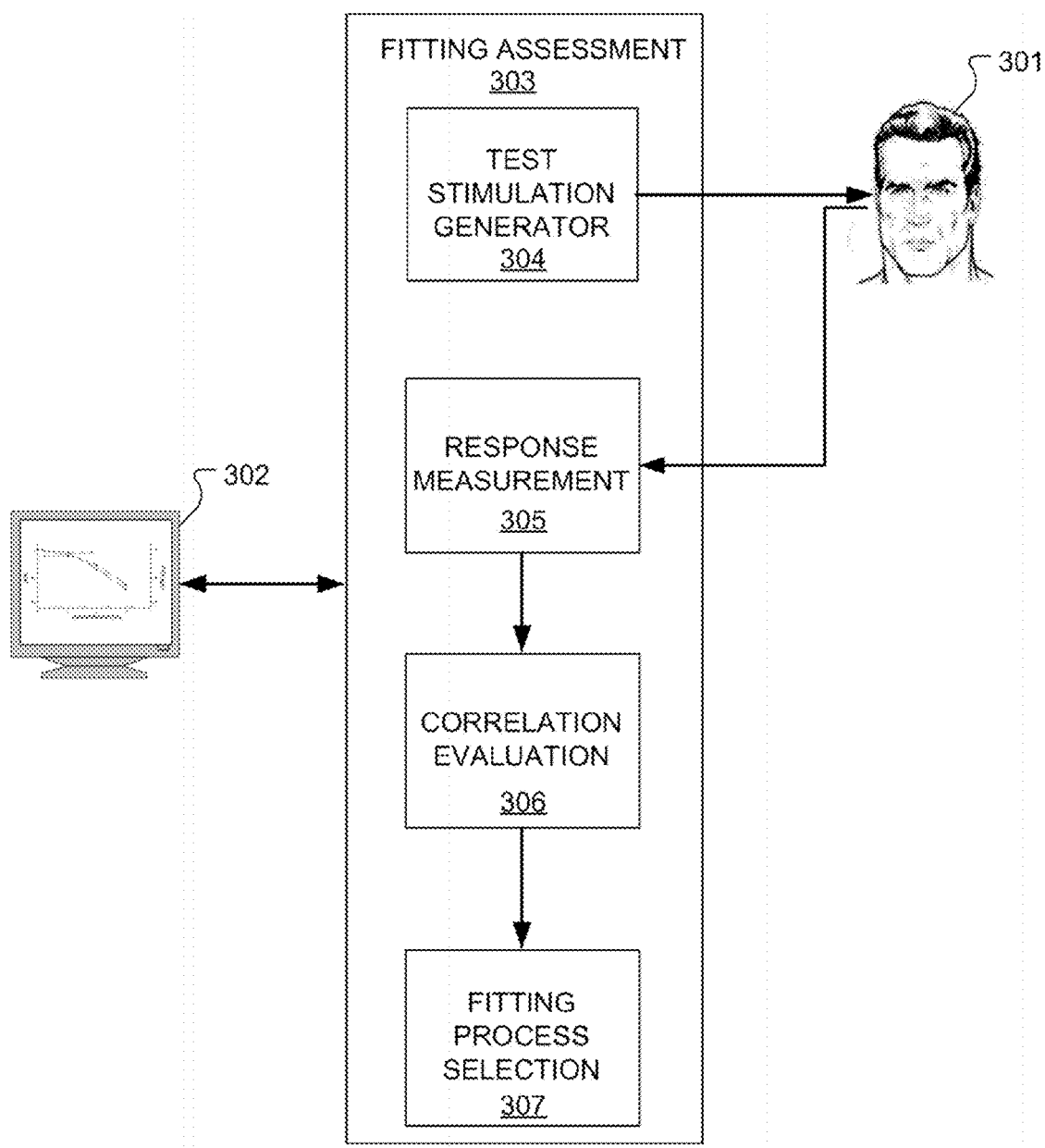
FIG. 3 shows various operational modules in a fitting assessment system according to an embodiment of the present invention.
Figure 4:
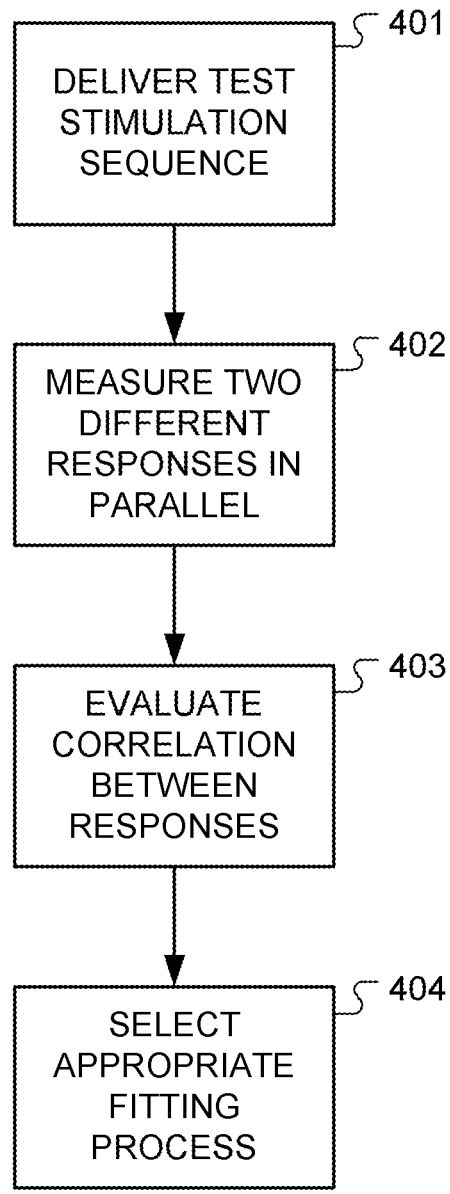
FIG. 4 shows various steps in a fitting assessment process according to an embodiment of the present invention.

FIG. 3 shows various operational modules in a fitting assessment system and FIG. 4 shows various steps in a fitting assessment process according to embodiments of the present invention. The fitting assessment system 303 includes a test stimulation generator 304 that delivers to the cochlear implant patient 301 a test stimulation sequence at a given test frequency, step 401. The test stimulation sequence from the test stimulation generator 304 includes alternating stimulation periods of jittered stimulation in which the test frequency varies due to a jitter variation component, and unjittered stimulation in which the test frequency is constant without a jitter variation component.

Figure 5:
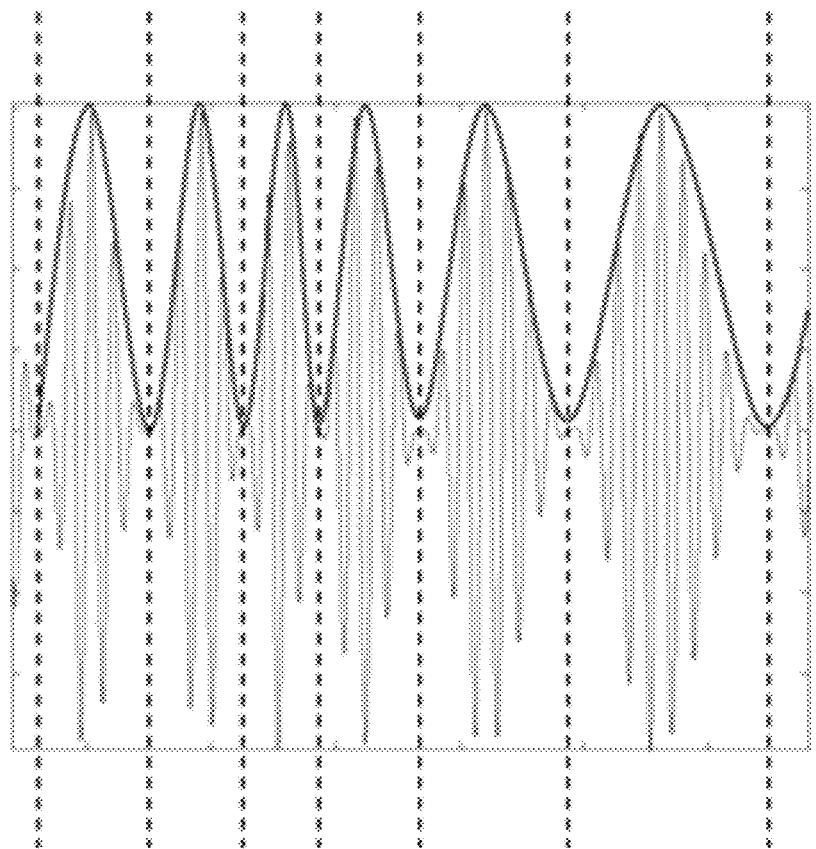
FIG. 5 shows an example waveform for a jittered AASSR stimulus sequence.

For each fitting assessment session, the duration of the test stimulation sequence produced by the test stimulation generator 304 should be long enough to properly establish the physiological steady-state response in the test person; typically about 30 seconds. However, this value is dependent on various parameters and may be patient specific, so any value between 15 and 60 seconds or even more than 60 seconds may be acceptable. The test stimulation generator 304 may specifically deliver an acoustic and/or electric test stimulation sequence to the cochlear implant patient 301. FIG. 5 shows an example waveform for a jittered AASSR stimulus sequence. In various specific embodiments, the jitter variation component produced by the test stimulation generator 304 may create a constant amount of variation in the test frequency during all of the jittered stimulation periods, or it may change the amount of variation in the test frequency between different jittered stimulation periods, and a Gaussian jitter variation component may specifically include standard deviations from 0.2 to 0.8, more specifically from 0.4 to 0.6. A test stimulation sequence may comprise of purely jittered, purely unjittered or any mix of jittered and unjittered stimulation periods.

The test stimulation generator 304 may deliver stimulation periods with uniform time durations, or stimulation periods with different time durations. It may be advantageous for the test stimulation generator 304 to deliver jittered stimulation periods and unjittered stimulation periods that have the same duration in time so that the auditory system of the cochlear implant patient 301 always has the same time to adapt to a new test stimulation sequence. In case of EASSR that requirement can be fulfilled quite easily, but for AASSR, it may be advantageous to meet another additional requirement in addition. In the jittered stimulation period shown in FIG. 5, the vertically dashed lines separate full sinusoidal wave cycles within the jittered stimulation period. The specific lengths of the individual full wave cycles may vary depending on the specific amount of the jitter variation component. It may be advantageous for AASSR to use only jitter variation patterns that include such full wave cycles so that an entire jittered stimulation period contains multiple full wave cycles.

A response measurement module 305 in the fitting assessment system 303 measures in parallel at least two different responses of the cochlear implant to the test stimulation sequence, step 402. The response measurement module 305 includes an objective measurement submodule that measures an objective electrophysiological response of the cochlear implant patient 301 (e.g., an auditory steady-state response (ASSR) such as an acoustically evoked ASSR (AASSR) and/or an electrically evoked ASSR (EASSR)), and a subjective measurement submodule that measures a subjective psychophysical response of the cochlear implant patient 301 (e.g., based on perception by the cochlear implant patient 301 of the jitter variation component).

A correlation evaluation module 306 evaluates a correlation between the different responses, step 403, to determine an appropriate fitting process for the cochlear implant patient 301, step 404. To that end, the correlation evaluation module 306 may include a fitting process selection submodule that determines an objective electrophysical fitting process as the appropriate fitting process when the correlation is evaluated to be sufficient. When the correlation evaluation module 306 evaluates the correlation to be insufficient, the fitting process selection submodule may further determine a subjective psychophysical fitting process as the appropriate fitting process.

It is important to test the cochlear implant patient with a test stimulation sequence that includes multiple periods of jittered stimulation and unjittered stimulation to allow the patient to subjectively respond and indicate detection of a jittered stimulation period at the same time that an objective electrophysiologic measurement is performed.

Figure 6:
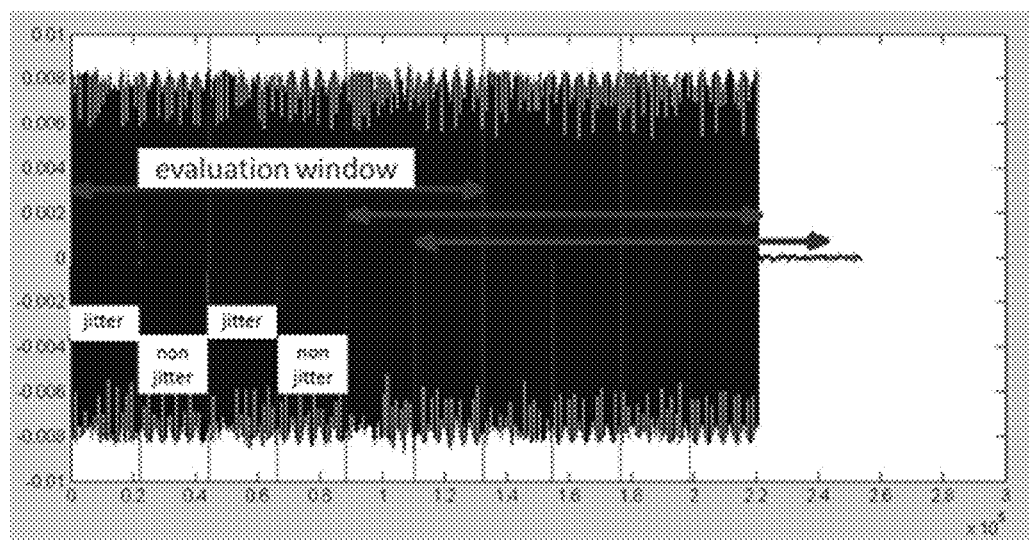
FIG. 6 shows an example of a recorded test signal for a test stimulation sequence containing jittered and unjittered stimulation periods.

For the ASSR signal measurement, an electroencephalogram (EEG) signal can be recorded in response to either an acoustic test stimulation sound source (in the case of AASSR) or an electrical test stimulation sound source (the cochlear implant electrode contacts in the case of EASSR). The analysis window may be shifted in time for the calculation of the ASSR signal. The EEG signal can be measured using implantable or non-implantable recording electrodes, for example, on the scalp and/or the forehead of the patient. FIG. 6 shows an example of an ASSR response recording as a function of recording time (ms) for a test stimulation sequence that contains jittered and unjittered stimulation periods.

Figure 7:
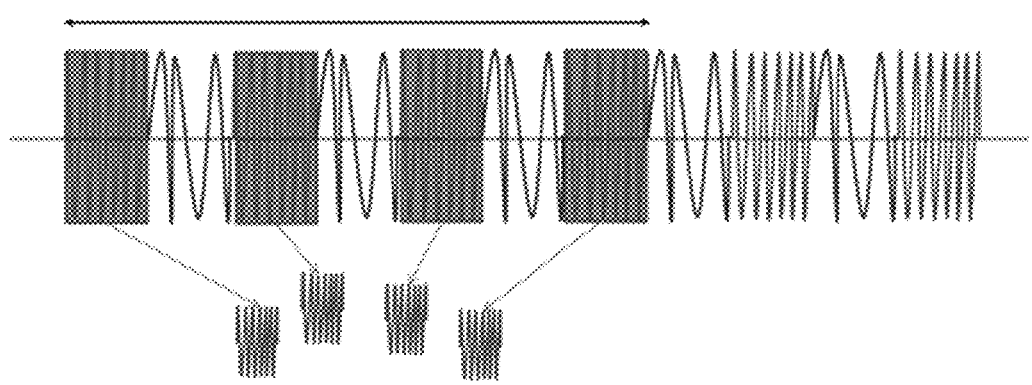
FIG. 7 shows a schematic EEG signal in response to jittered and unjittered stimulation periods.

In order to derive the ASSR signal out of the recorded EEG signal, an evaluation window can defined with a length L, wherein L is at least time T. If lengths L of both the jittered and unjittered stimulation periods are not equal, then the length of the evaluation window should be at least the length of the shortest jittered/unjittered stimulation period within the test stimulation sequence. FIG. 7 shows an EEG signal where the evaluation window extends over 4 jittered/unjittered stimulation periods. The evaluation window may be chosen such that each second period T out of the EEG signal is chosen for further processing (in particular, if a test stimulation sequence includes only identical unjittered stimulation periods). Alternatively, just a single stimulation period may be chosen out of the signal. The filtered data for the chosen stimulation period(s) are then further processed, for example, by averaging the filtered data, calculating a frequency spectrum (e.g. by FFT) of the averaged data, and then deriving the FFT amplitude at $f_c-f_m$ or $f_c+f_m$. Then, the evaluation window can be shifted in time, the evaluation procedure repeated.

Figure 8:
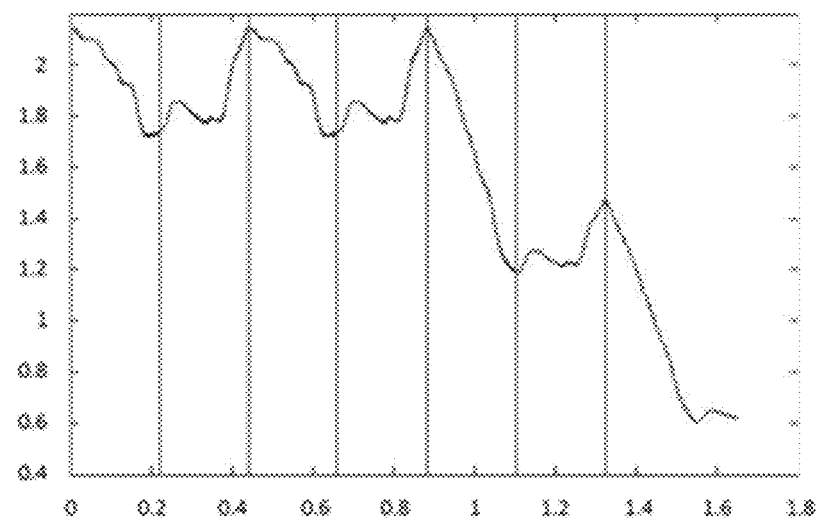
FIG. 8 shows an example waveform of an FFT test analysis.

FIG. 8 shows an example waveform of an FFT test analysis for simulated EASSR values (unnormalized) as a function of time (corresponding to the shifting of the analysis window). The vertical lines indicate the changes between jittered and unjittered stimulation periods. As can be seen in FIG. 8, there will be local maximums and minimums in the measured ASSR signal. Local maximums correspond to when the evaluation window is in a position where it discards all jittered stimulation periods so that only unjittered stimulation periods are taken for averaging and FFT analysis. Similarly, local minimums correspond to when the evaluation window is in a position where it discards all unjittered stimulation periods. The sequence of local maxima and minima in the ASSR signal can be assigned to the specific points of the EEG signal, and further to the test simulation sequence where jittered and unjittered stimulation periods have changed. Thus the beginning of the recording can be identified which previously was unknown because of the unknown delay between the test stimulus sequence and the start of the response signal recording. This knowledge is used for the comparison of this objective electrophysical measurement with the result of the subjective psychophysical test.

In the specific case of EASSR measurements, cancellation of the stimulus artifacts also needs to be considered. Possible methods are suggested by Hoffman and Wouters, *Electrically Evoked Auditory Steady State Responses in Cochlear Implant Users*, J Assoc Res Otolaryngol. 2010 June, 11(2): 267-82 and Hoffman and Wouters, *Improved Electrically Evoked Auditory Steady-State Response Thresholds in Humans*, J Assoc Res Otolaryngol. 2012 August, 13(4):573-89; which are incorporated herein by reference in their entireties.

In the subjective psychophysical test that is performed in parallel to the ASSR recording, a test patient may be asked to differentiate between jittered and unjittered stimulation periods (the perceived signal sounds different). The patient reports when he detects a jittered stimulation period is occurring, or the patient may count the number of jittered stimulation periods. One possible test scenario might be as follows:

Two unjittered tones with different pitches are presented to the test person.

The difference in pitch is increased such that this person can reliably discriminate the two pitches (e.g. discrimination rate is higher than 90%).

A test stimulation sequence as described above then is presented with jittered stimulation periods and the test person has to indicate if he still can discriminate the two tones. Alternatively, the task of the test person may be to report which of the two pitches he/she has perceived as higher.

Then another test stimulation sequence is presented with increased jitter compared to the previous stimulation stream.

Breaks between the test stimulation sequences are optional.

Various other psychophysical tests are feasible, these are just some examples.

Figure 9:
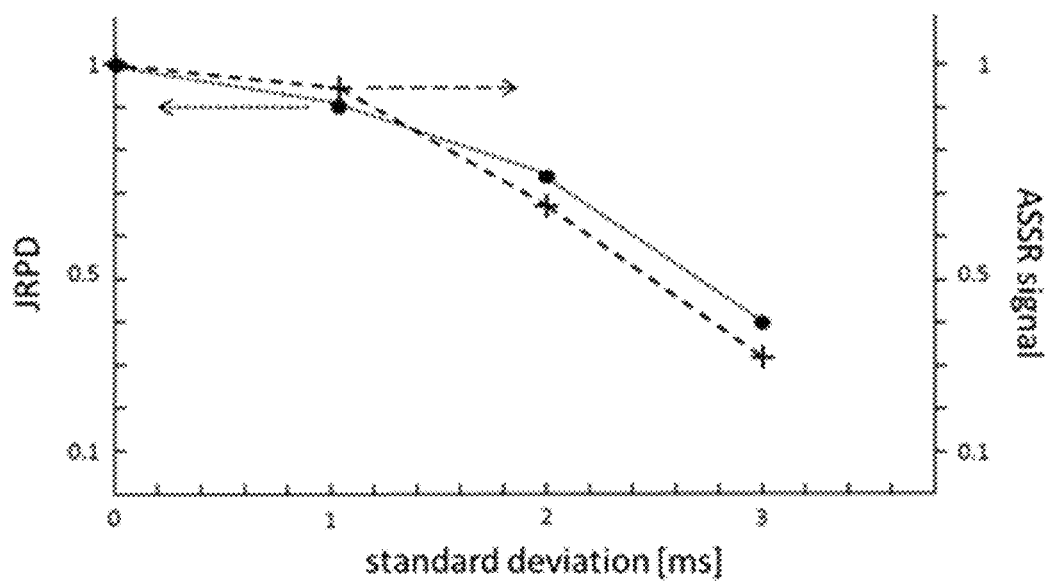
FIG. 9 shows an example schematic of the correlation between ASSR and jittered pitch rate discrimination (JRPD).

In the subjective psychophysical test, the tested patient generally has to provide what is known as a jittered rate pitch discrimination (JRPD). FIG. 9 shows one set of experimental results which indicates that the JRPD decreases with increased standard deviation. Subsequently, the values of the ASSR and the JRPD are normalized (e.g. so that the distance of maximum and minimum ASSR value is 1, and the JRPD for pure unjittered stimulation is 1), and then compared in terms of various correlations, e.g. both values are plotted in one graphic against the standard deviation of the jittered signal (FIG. 9). Possible correlation criteria might include common peaks, same monotony of the recorded signals, sum of means square of distances between corresponding points are below a specific value, etc. If a correlation between both signals can be shown, this correlation may serve as a reference for subsequent electrophysiological measures or fitting procedures, e.g. based on ASSR as an objective measurement. If the pre-test does not show a correlation between both entities a standard psychophysical fitting procedure has to be employed.

In the following the implementation of simultaneous objective measurements and subjective tests together is described. This implementation is exemplary described for AASSR.

ASSR requires the presentation of a stimulus signal having temporal periodicity. In AASSR the test stimulus signal may be a sinusoidal amplitude modulated signal (SAM) having a carrier frequency $f_c$ modulated by some frequency modulation component $f_m$, as shown in FIG. 10A, with FIG. 10B showing the result in the frequency domain for FFT. In the case of EASSR, the presentation of a train of bi-phasic pulses, for example is modulated by $f_m$. By means of standard EEG measurement the ASSR signal may be determined and characterized. On the other hand, subjective psychophysical pitch discrimination tests require the presentation of two or more rather short test pulses, e.g. individual bi-phasic pulses. This test requires the cooperation of the test person and information of his/her subjective perception.

Simultaneous measurements may be performed by adding a jitter c to the stimulus signal, and the stimulus signal may be adapted to avoid artifacts in the ASSR signal at frequencies around the modulation frequency $f_m$. FIG. 11A shows the carrier frequency of the SAM being modulated by $f_m+\epsilon$, wherein c may be any value out of $[-\epsilon_1,+\epsilon_1]$ and may be varying within these boundaries in the stimulus signal of a single test session. FIG. 11B shows the frequency domain FFT of that operation, where the effects of the jitter component are more readily apparent. In order to perform simultaneous objective measurement of ASSR and subjective psychophysical pitch discrimination tests, a compromise must be found regarding the length of the stimulus signal.

Jitter affects/reduces the periodicity in the recorded EEG signal and therefore deteriorates/reduces the amplitude of the extracted ASSR signal. Presenting jittered test stimuli also reduces pitch discrimination because it becomes more difficult for the test person to discriminate the individually presented pitches. Varying the amount of jitter, i.e. varying the interval $[-\epsilon_1,+\epsilon_1]$, in subsequent test sessions may be useful for finding whether there is a correlation between both test methods and further whether objective ASSR measurement may be considered as the sole fitting method or at least as a further contribution to the fitting of the test person.

Figure 12:
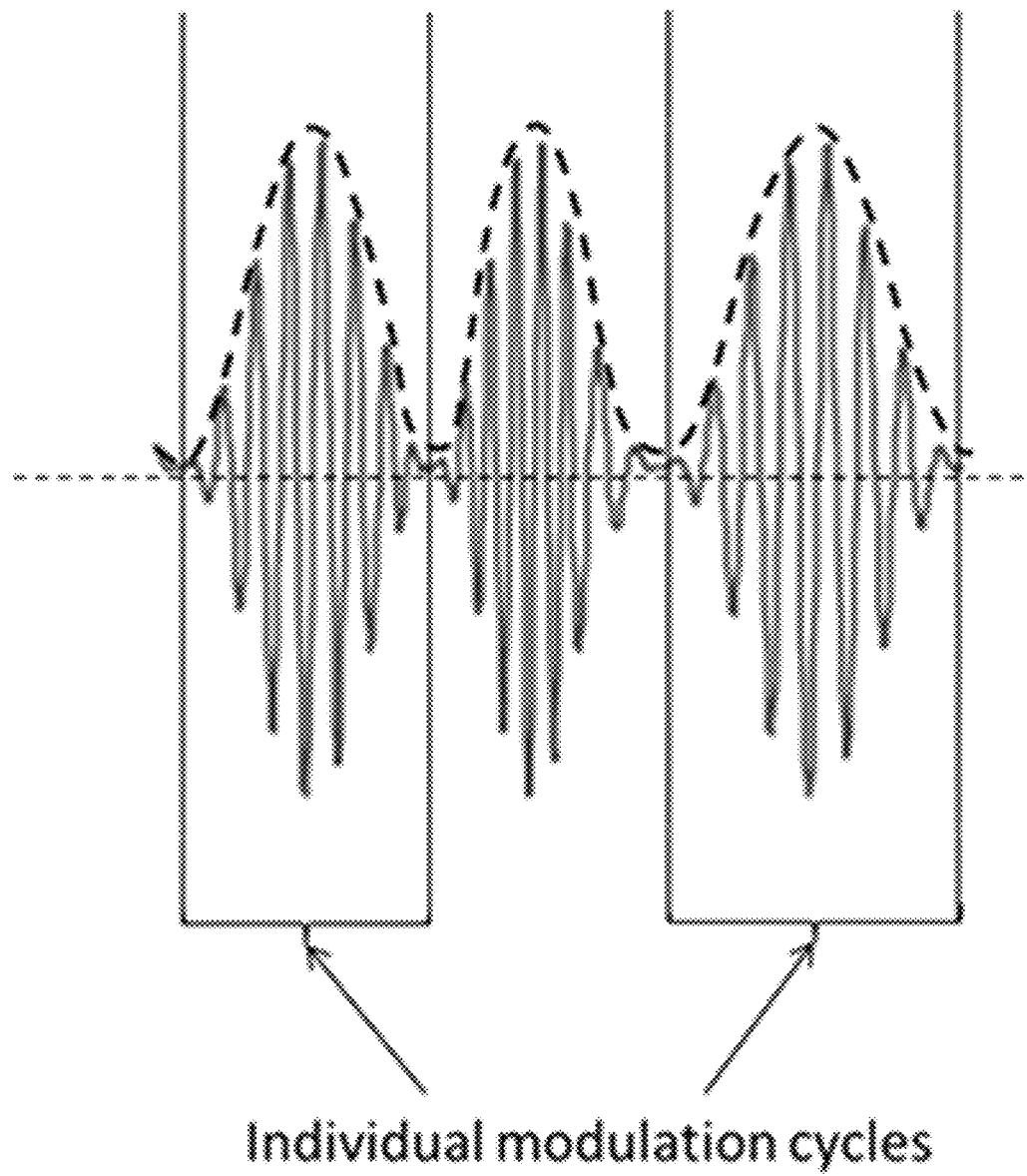
FIG. 12 shows an example of multiple sequential SAM signals.

One straightforward way to perform such simultaneous measurements would be in case of AASSR to generate a SAM stimulus train composed of individually jittered SAM signals k with added jitter components $\epsilon$ from $[-\epsilon_k,+\epsilon_k]$. Each jittered SAM signal k may have a duration of one or an integer multiple of a modulation cycles corresponding to $f_m\pm\epsilon$. FIG. 12 shows an example of multiple sequential SAM signals k, which may be generated, for example, by a soundcard of a computer workstation. The upper dashed line in FIG. 12 shows the envelopes of each modulation cycle (where there is constant c within each cycle) of the jittered SAM signals. The SAM envelopes can be represented by sine waves with constant frequencies $\omega_k$; i.e. proportional to $\sin(\omega_k*t)$. The whole SAM stimulus sequence therefore can be represented as a composition of k individual modulations cycles, all having different or equal but constant frequencies $\omega_k$.

Figure 13A:
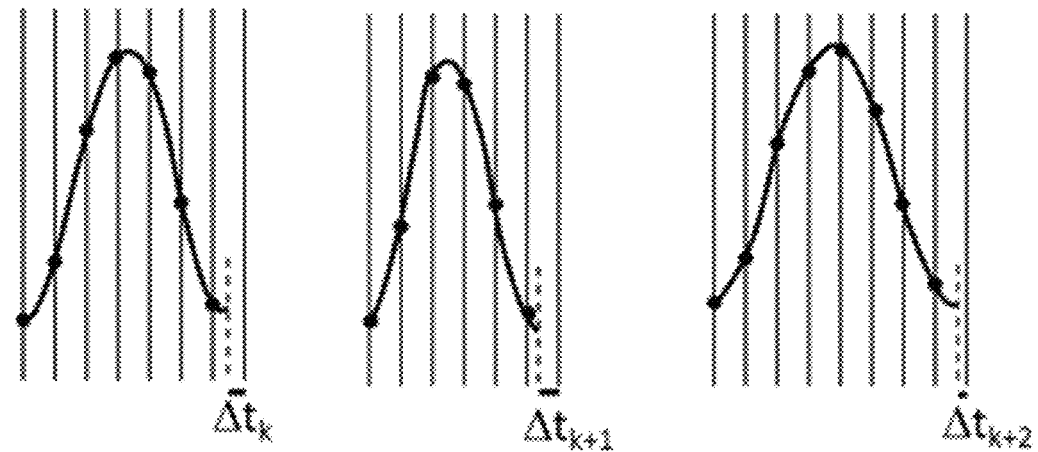
FIG. 13 A-B shows the time offset deltas that arise from sampling of the SAM envelopes.

Before the SAM stimulus train of analog jittered SAM signals can be presented to a test person in a fitting process, it has to be A/D converted into a corresponding digital stimulus signal. An A/D converter operates with a specific sampling rate, which for cochlear implant applications are typically in the high kHz range. This sampling frequency is a fixed number during operation and, therefore, the corresponding sampling period t is usually not an integer multiple of an individual modulation cycle. This problem is illustrated in FIG. 13A where the solid vertical lines indicate the sampling periods of the A/D converter (and the dots represent the sampled values). The time mismatch delta $\Delta t$ towards the lower right of each example waveform indicates the amount of mismatch between the length of a modulation cycle and the next larger integer multiple of the sampling period. And since the sampling period of the A/D converter is unrelated to the length of the modulation cycles of the SAM stimulus train, each modulation cycle k may end with another (different) time mismatch delta $\Delta t_k$.

However, it has been discovered that these uncontrolled time mismatch deltas $\Delta t_k$ degrade the AASSR signal and adversely influence the simultaneous comparison between AASSR measurement signal and psychophysical pitch rate measurements. In addition, these uncontrolled time mismatch deltas $\Delta t_k$ also cause an artifact around the modulation frequency $f_m$.

Embodiments of the present invention propose an alternative approach and include systems and methods for fitting a cochlear implant system to an implanted patient. For example, in terms of the fitting assessment system shown in FIG. 3, the test stimulation generator 304 is configured to deliver to the implanted patient 301 a test stimulation sequence that is based on a concatenated sequence of time shifted envelopes corresponding to SAM signals that have a carrier frequency $f_c$ modulated by a jittered modulation frequency $f_m+\epsilon$, where c is a frequency jitter component selected from a jitter range of $[-\epsilon_1,+\epsilon_1]$. The response measurement module 305 is configured to measure patient responses to the test stimulation sequence including an auditory steady-state response (ASSR) measurement signal (e.g., specifically, an AASSR or EASSR arrangement) and a psychophysical pitch discrimination response. The test stimulation generator 304 is configured to adapt the time shifted envelopes to avoid measurement artifacts in the ASSR measurement signal around the modulation frequency $f_m$.

Typically, the test stimulation generator 304 is configured to derive the test sequence by an analog-to-digital sampling of the time shifted envelopes at a given sampling frequency having a corresponding sampling period. And the test stimulation generator 304 time shifts each envelope to offset a time mismatch delta representing a time difference for each preceding envelope between duration of the envelope and a next higher integer multiple of sampling.

Figure 13B:
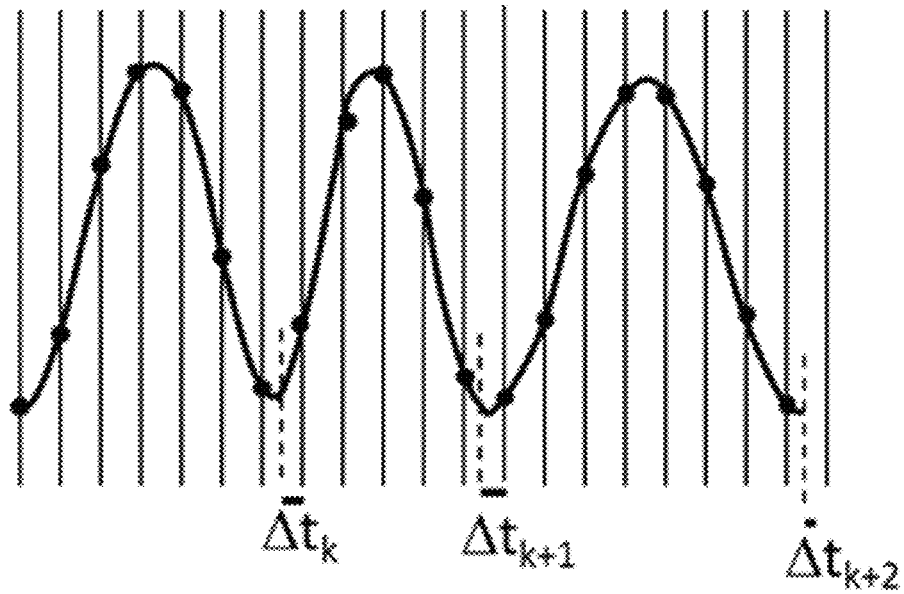
Figure 14:
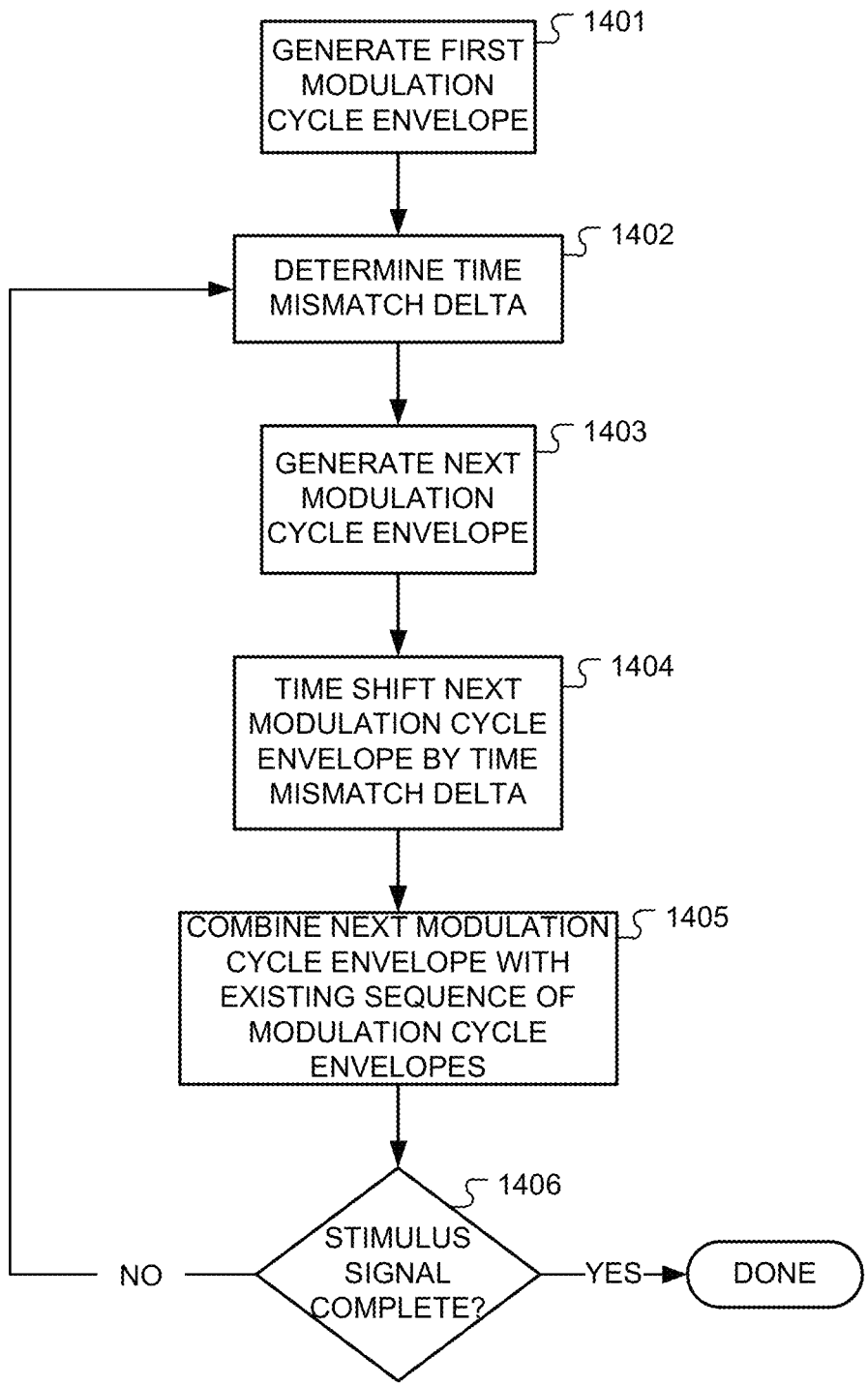
FIG. 14 shows various steps in a fitting process according to an embodiment of the present invention.

FIG. 14 shows various steps in a fitting process according to an embodiment of the present invention. Initially, a first modulation cycle k=1 is generated, step 1401, and its time mismatch delta $\Delta t_1$ is determined, step 1402. Then the next modulation cycle k=2 envelope is generated, step 1403, and time shifted relative to the preceding one (k=1) by a first time mismatch delta $\Delta t_1$, step 1404. The time shifted envelope is then combined with the prior existing sequence of modulation cycle envelopes, step 1405, and if the stimulus signal is not yet complete, step 1406, the process loops back to redetermine the accumulated time mismatch delta, step 1402, and shifted relative to its preceding ones (k=1 and k=2) by $\Delta t_1+\Delta t_2$, and generate the modulation cycle envelope for the next cycle k=3, returning to step 1403. In general, a $k^{th}$ modulation cycle k may be generated and shifted relative to the preceding ones (k=1 to k−1) by an accumulated time mismatch delta $\Delta t_1+\Delta t_2+\ldots+\Delta_{k-1}$. FIG. 13B shows one specific example of combined time shifted modulation cycle envelopes according to such a process.

The test stimulation generator 304 combines the time shifted modulation cycles to form a concatenated train of modulation cycles, which have a length of a full period (or an integer multiple of a full period) of a sine wave and at the same time avoid unwanted introduction of distortions caused by the sampling period of the A/D converter (which introduces unwanted jitter). In order to construct a full SAM stimulus train the test stimulation generator 304 multiplies this stimulus sequence by the carrier frequency $f_c$ (which determines the tonotopic location of the presented stimulus in the cochlea) and digitizes the SAM stimulus train in the A/D converter for output to the implanted patient being fitted.

As further shown in FIG. 3, specific embodiments may also include a correlation evaluation module 306 that is configured to evaluate a correlation between the patient responses to determine an appropriate fitting process for the cochlear implant patient. The correlation evaluation module 306 may include a fitting process selection sub-module 307 that is configured to determine an objective ASSR fitting process as the appropriate fitting process when the correlation is evaluated to be sufficient and/or a subjective psychophysical pitch discrimination fitting process as the appropriate fitting process when the correlation is evaluated to be insufficient.

A pseudo code representation of a specific embodiment might be set forth as follows:

```
Process Adaptive_SAM_Fitting
sp1=[ ],jitterz=0, u=0;
while length (sp1) <=duration*Fs
    %concatenate until duration is reached
fmi=fmspj (jitterz+1);
    %vector of modulation frequencies
jitterz=jitterz+1;
    %next modulation frequency
t=(u:1/Fs:(1/fmi));
sp1=[sp1 1+cos(2*pi*fmi*t+pi)];
    %concatenate modulation cycles
u=1/Fs−mod(1/fmi−u,1/Fs);
end
```

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A fitting system for fitting a cochlear implant system implanted in a patient, the system comprising:
   a test stimulation generator configured to deliver to the patient a test stimulation sequence based on a concatenated sequence of time shifted envelopes of sinusoidal amplitude modulated (SAM) signals having a carrier frequency fc modulated by a jittered modulation frequency $f_m+\epsilon$, where $\epsilon$ is a frequency jitter component selected from a jitter range of $[-\epsilon_1,+\epsilon_1]$; and
   a response measurement module configured to measure patient responses to the test stimulation sequence including an auditory steady-state response (ASSR) measurement signal and a psychophysical pitch discrimination response;
   wherein test stimulation generator is configured to adapt the time shifted envelopes to avoid measurement artifacts in the ASSR measurement signal around the modulation frequency $f_m$.

2. The system according to claim 1, wherein the test stimulation generator is configured to derive the test sequence by an analog-to-digital sampling of the time shifted envelopes at sampling frequency having a corresponding sampling period.

3. The system according to claim 2, wherein the test stimulation generator is configured to time shift envelopes of the SAM signals to offset a time mismatch delta representing an accumulated time difference for all preceding envelopes between each envelope duration and a next higher integer multiple of sampling period.

4. The system according to claim 1, further comprising:
a correlation evaluation module configured to evaluate a correlation between the patient responses to determine an appropriate fitting process for the patient.

5. The system according to claim 4, wherein the correlation evaluation module includes a fitting process selection sub-module configured to determine an objective ASSR fitting process as the appropriate fitting process when the correlation is evaluated to be sufficient.

6. The system according to claim 4, wherein the correlation evaluation module includes a fitting process selection module configured to determine a subjective psychophysical pitch discrimination fitting process as the appropriate fitting process when the correlation is evaluated to be insufficient.

7. The system according to claim 1, wherein the ASSR measurement signal is an acoustically evoked ASSR (AASSR).

8. A method for use in fitting a cochlear implant system implanted in a patient, the method comprising:
delivering to the patient a test stimulation sequence based on a concatenated sequence of time shifted envelopes of sinusoidal amplitude modulated (SAM) signals having a carrier frequency $f_c$ modulated by a jittered modulation frequency $f_m+\epsilon$, where $\epsilon$ is a frequency jitter component selected from a jitter range of $[-\epsilon_1, +\epsilon_1]$; and
simultaneously measuring patient responses to the test stimulation sequence including an auditory steady-state response (ASSR) measurement signal and a psychophysical pitch discrimination response;
wherein the time shifted envelopes are adapted to avoid measurement artifacts in the ASSR measurement signal around the modulation frequency $f_m$.

9. The method according to claim 8, wherein the test sequence is derived by an analog-to-digital sampling of the time shifted envelopes at sampling frequency having a corresponding sampling period.

10. The method according to claim 9, wherein each SAM envelope is time shifted to offset a time mismatch delta representing a time difference for each preceding SAM envelope between duration of the SAM envelope and a next higher integer multiple of sampling period.

11. The method according to claim 8, further comprising:
evaluating a correlation between the patient responses to determine an appropriate fitting process for the patient.

12. The method according to claim 11, further comprising:
determining an objective ASSR fitting process as the appropriate fitting process when the correlation is evaluated to be sufficient.

13. The method according to claim 11, further comprising:
determining a subjective psychophysical pitch discrimination fitting process as the appropriate fitting process when the correlation is evaluated to be insufficient.

14. The method according to claim 8, wherein the ASSR is an acoustically evoked ASSR (AASSR).

* * * * *